United States Patent [19]

Breidegam

[11] Patent Number: 4,745,519
[45] Date of Patent: May 17, 1988

[54] GROUNDING STRAP WHICH CAN BE MONITORED

[75] Inventor: Albert C. Breidegam, Sharpsburg, Ga.

[73] Assignee: Semtronics Corporation, Atlanta, Ga.

[21] Appl. No.: 2,172

[22] Filed: Jan. 12, 1987

Related U.S. Application Data

[63] Continuation-in-part of Ser. No. 804,052, Dec. 2, 1985, Pat. No. 4,639,825, which is a continuation-in-part of Ser. No. 654,636, Sep. 25, 1984, Pat. No. 4,577,256.

[51] Int. Cl.$^4$ .................................... H05F 3/00
[52] U.S. Cl. ..................................... 361/220; 361/212
[58] Field of Search ................. 361/212, 220, 223; 57/907; 324/51, 538–544

[56] References Cited

U.S. PATENT DOCUMENTS

| | | | |
|---|---|---|---|
| 1,531,862 | 3/1925 | Larned . | |
| 3,063,447 | 11/1962 | Kirsten | 128/134 |
| 3,377,509 | 4/1968 | Legge | 317/2 |
| 3,422,460 | 1/1969 | Burke et al. | 2/73 |
| 3,424,698 | 1/1969 | Lupinski et al. | 252/500 |
| 3,459,997 | 8/1969 | Legge | 317/2 |
| 3,541,389 | 11/1970 | Van Name | 317/2 |
| 3,582,448 | 6/1971 | Okuhasi | 161/87 |
| 3,596,134 | 7/1971 | Burke | 317/2 B |
| 3,699,590 | 10/1972 | Webber et al. | 2/73 |
| 3,812,861 | 5/1974 | Peters | 128/418 |
| 3,832,841 | 9/1974 | Cole | 57/152 |
| 3,851,456 | 12/1974 | Hamada et al. | 57/140 |
| 3,857,397 | 12/1974 | Brosseau | 128/384 |
| 3,904,929 | 9/1975 | Kanaya et al. | 317/2 |
| 3,949,129 | 4/1976 | Hubbard | 428/190 |
| 3,986,530 | 10/1976 | Maekawa | 139/425 |
| 3,987,613 | 10/1976 | Woods et al. | 57/140 |
| 4,267,233 | 5/1981 | Tanaka et al. | 428/389 |
| 4,321,789 | 3/1982 | Dammann et al. | 57/224 |
| 4,373,175 | 2/1983 | Mykkanen | 361/220 |
| 4,398,277 | 8/1983 | Christiansen et al. | 361/220 |
| 4,402,560 | 9/1983 | Swainbank | 339/11 |
| 4,420,529 | 12/1983 | Westhead | 428/244 |
| 4,422,483 | 12/1983 | Zins | 139/420 |
| 4,459,633 | 7/1984 | Vandermark | 361/220 |
| 4,475,141 | 10/1984 | Antonevich | 361/220 |
| 4,577,256 | 3/1986 | Breidegam | 361/212 X |
| 4,605,984 | 8/1986 | Fiedler | 361/220 |
| 4,639,825 | 1/1987 | Breidegam | 361/212 |
| 4,664,158 | 5/1987 | Sands | 139/422 |

FOREIGN PATENT DOCUMENTS 2547390 5/1977 Fed. Rep. of Germany .
1067260 8/1965 United Kingdom .

Primary Examiner—L. T. Hix
Assistant Examiner—David M. Gray
Attorney, Agent, or Firm—Kilpatrick & Cody

[57] ABSTRACT

A device for connecting a person to electrical ground comprising a stretchable grounding strap which may be worn on the arm or leg and has two or more sections of conductive material; one or more conductors connecting each section of conductive material to ground and circuitry to actuate warning indicators if any of the sections of conductive material are not contracting the wearer or if the connection between any section of conductive material and ground is open. The circuitry may also actuate an indicator if a safety resistor between a section of conductive material and ground is shorted.

22 Claims, 3 Drawing Sheets

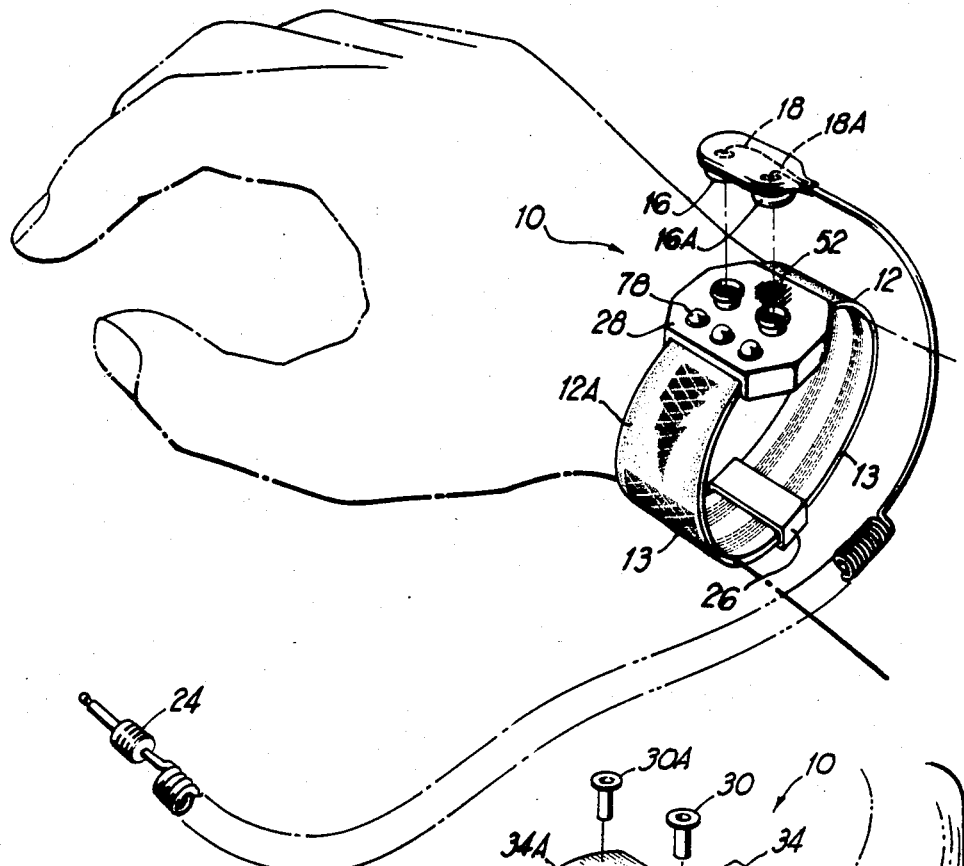
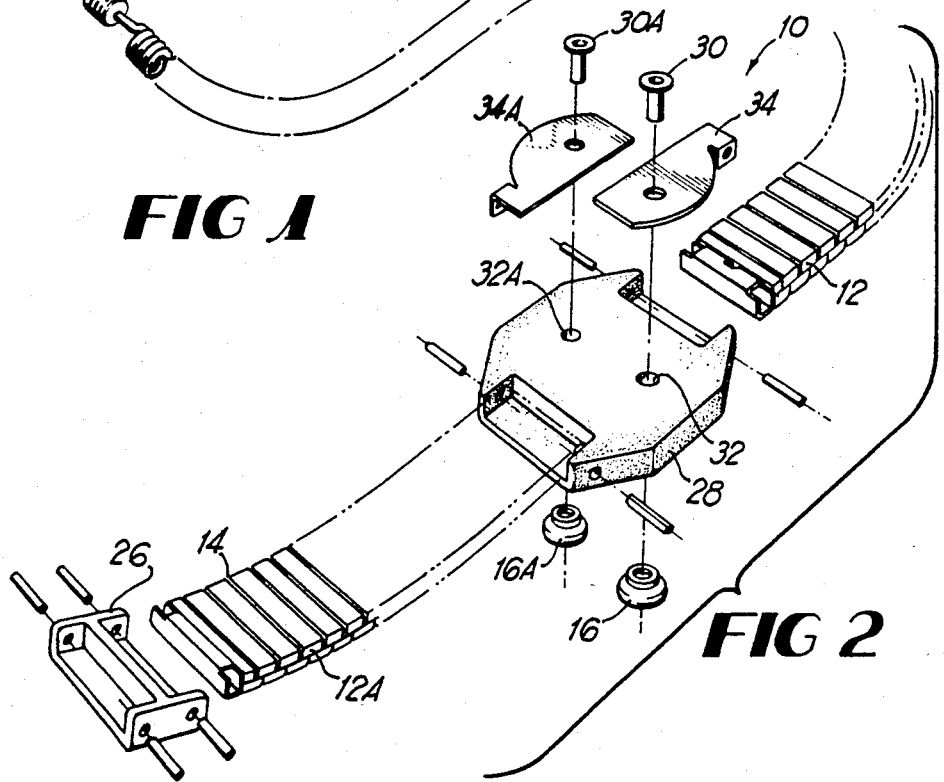

GROUNDING STRAP WHICH CAN BE MONITORED

This application is a continuation-in-part of my earlier application for United States Patent entitled, "STRETCHABLE GROUNDING STRAP HAVING REDUNDANT CONDUCTIVE SECTIONS" filed Dec. 2, 1985 and having Ser. No. 06/804,052, which is a continuation-in-part of my earlier application for United States Patent entitled "WOVEN STRETCHABLE GROUNDING STRAP" filed Sept. 25, 1984 and having Ser. No. 06/654,636, now U.S. Pat. No. 4,577,256.

BACKGROUND OF THE INVENTION

This invention relates to a strap that may be comfortably worn on the arm or leg, that has two or more sections of conductive material for improved wicking of static electrical charges from the wearer's body and that has or is connected to circuitry that activates audible or visual indicators if certain failure conditions exist.

Static electricity causes problems in the electronics and other industries, particularly with the advent of integrated circuits and other microelectronic components. Components such as integrated circuits, for example, may be disabled or destroyed by over-voltages or power density resulting from static electricity. Certain junctions in such circuits can be destroyed by as little as a 50-volt potential, which radically changes the doping structure in their lattices. Power densities resulting from excessive potential and imperfections in circuit layout or structure can vaporize or radically alter the silicon substrate and thus impair or destroy a circuit's performance. Yet a person walking on carpet on a dry day can accumulate as much as 30,000 volts of potential, and he can triboelectrically generate thousands of volts by simply changing his position in his chair or handling a styrofoam cup.

Such a person can inadvertently discharge such static potential into a circuit or component by touching it and causing over-voltage or excessive power density. Additionally, the potential in such a person's body can induce a charge in a circuit that can later cause over-voltage or excessive power density when the circuit is subsequently grounded.

More and more frequently, therefore, those in industries in which integrated circuits and other microelectric components are handled or assembled are taking measures to limit the failure rate of those circuits and components by attempting to keep them as well as their environment at zero electrical potential. Such measures include providing workers and work stations with anti-static carpet, conductive or dissipative grounded desk top work surfaces, hot air ion generators which emit ions to neutralize static charges, and grounding straps to keep workers at zero potential.

The term "conductive" herein, and according to its customary usage in the art, means an electrical resistence of between 0 and $10^5$ ohms. Similarly, "dissipative" means a resistence of between $10^5$ and $10^9$ ohms, "anti-static" means a resistence of between $10^9$ and $10^{14}$ ohms and "insulative" means a resistence of more than $10^{14}$ ohms.

The situations in which grounding straps are used heighten the importance of their being reliable in maintaining continuous electrical contact with the skin. The person working on microelectronic components for integrated circuits may be completely unaware that he has accumulated minor static electrical charges, and may therefore unknowingly be in a position to disable circuits on which he is working or which he is handling. If his strap is lose or he has removed it, he may be unaware that electrical discharges transmitted from his fingers are disabling the circuits. (A typical person cannot sense a static electrical discharge of less than approximately 3,500 volts.) No one may discover that the circuits have been disabled or damaged until hours, days or weeks later, when the circuits have been placed in components or devices which fail in the field. Removal and repair or replacement of the circuits once in the field is far costlier than avoiding potential failure while the wearer is handling the circuits. Thus, the wearer's employer typically must depend upon the effectiveness of the wrist strap to maintain a lower failure rate of such electronic circuits and components by ensuring that the strap maintains continuous electrical contact with the wearer's wrist.

These considerations have been addressed by several types of grounding straps. U.S. Pat. No. 4,373,175 issued Feb. 8, 1983 to Mykkanen, for instance, discloses an extensible metal band similar to a "Speidel" watch band on which a snap fastener for a grounding cord is attached. Such a strap includes only one contact and line connecting the strap with ground, however, and its conductive metal outer surface can prove dangerous to the wearer if it contacts an electrical potential sufficient to electrocute the wearer. Further, the Mykannen strap includes no visual or aural means to inform the wearer or others when the strap loses electrical connection with ground.

Another grounding strap is disclosed in U.S. Pat. No. 3,857,397 issued Dec. 31, 1984 to Brosseau. Outer and inner conductive polyolefin layers sandwich an intermediate nylon scrim layer to form the band. Hook and loop (Velcro) fastening material holds the strap on the wrist. This strip is typical of a number of straps having carbon-suffused synthetics or other conductive polyolefins. Body oils and minerals can accumulate on such surfaces and interfere with electrical contact between the band and the skin. Further, the Brosseau strap includes only one electrical contact surface and grounding, and that patent discloses no visual or aural means to inform the the wearer or others of failure conditions.

Another approach to many of these problems is disclosed in U.S. Pat. No. 4,398,277 issued Aug. 9, 1983 to Christiansen and Westberg. This strap is made of knitted stretchable fabric containing stainless steel fibers. A plastic and metal fitting permanently closes the strap into a loop of predetermined size and has a connection for a grounding cord. As in the case of the straps mentioned above, the Christiansen strap includes only one electrical contact surface and grounding line, and no visual or aural means is disclosed for informing the wearer of failure conditions.

SUMMARY OF THE INVENTION

The present invention includes a stretchable grounding strap with two or more separate actions of conductive material, one or more conductors connecting each section of conductive material to ground and circuitry to actuate warning indicators if any of the sections of conductive material are not connected to the wearer's body or if the connection between any section of conductive material and ground is open. The circuitry may also actuate indicators if a safety resistor between a section of conductive material and ground is shorted.

The strap utilizes a stretchable material having two or more electrically conductive sections on its inner surface. In one group of embodiments, the conductive sections are of metallic or conductive fibers, and face yarns on the outer surface may form letters words, logos or other pleasing or commercially attractive designs. Elastic yarns allow the material to stretch easily and comfortably. One or more clasps are attached to the material. Fittings are mounted on the clasps, one fitting corresponding to each section of conductive material, to receive grounding conductors. In a second group of embodiments, a plurality of metallic links separated into sections by nonconductive materials form the expandable strap and are nonconductive on their outer surface.

The fittings corresponding to each section of conductive material on the straps are each connected to ground by an electrical conductor. This conductor may be, for instance, an electrically conductive line or cord.

The circuit of the present invention monitors at least two parameters for failure and actuates indicators when failure occurs. First, the circuit monitors the connections between it (and thus the conductive sections of the strap) and ground to actuate indicators when any of those connections are open. Second, the circuit monitors the connections between it and the conductive sections of the strap to actuate indicators when the conductive sections of the strap are not connected to the wearer's body. The circuit may also monitor the connections between it and ground or the conductive sections of the strap, which paths contain a 1 megohm or greater safety resistor, to actuate indicators when the resistor or resistors are shorted.

A preferred embodiment of the circuit performs this monitoring function by measuring resistances. This circuit is located electrically between the safety resistor or resistors and the sections of conductive material on the strap. The circuit is ideally suited for miniaturization so that it may be placed in the strap clasp. The circuit actuates a visual and aural indicator if the resistance of the loop comprising the conductors between the circuit and ground reaches a certain value indicating an opening in the loop and thus a break in one of the paths between the circuit and ground. It also actuates visual and aural indicators if the resistance of the loop comprising the connection between the circuit and a wrist strap conductive section, the path between the wrist strap conductive sections and another connection between another wrist strap conductive section and the circuit reaches or exceeds a certain value indicating that one of the conductive sections has lost contact with the wearer's body. The circuit may further actuate visual and aural indicators if the resistance in the loop comprising the paths between the circuit and ground, at least one of which contains a safety resistor, reaches or falls below a certain value, indicating that one of the safety resistors has shorted.

The warning indicators may take the form of light emitting diodes, liquid crystal display, bulbs or other suitable visual indicators, as well as piezoelectric buzzers or screamers or other suitable aural displays. These indicators may be located conveniently on the strap clasp or at other appropriate locations in the wearer's vicinity, or they may be located remotely at a central monitoring station or other suitable location for centralized monitoring.

It is therefore an object of this invention to provide an inexpensive monitorable stretchable grounding strap that has at least two sections of electrically conductive material, each of which may be independently connected to ground for additional reliability.

It is an additional object of this invention to provide an inexpensive monitorable stretchable grounding strap with related circuitry which gives a visual and aural warning when the circuitry senses loss of electrical ground, loss of contact between one or more of the conductive sections of the strap and wearer's body, or shorting of a safety resistor.

It is an additional object of this invention to provide a grounding strap monitoring device comprising circuitry that may be conveniently located on the grounding strap and that monitors performance of the strap and its electrical connection with ground.

It is an additional object of this invention to provide a grounding strap monitoring device which comprises circuitry that actuates indicators on the strap or at another appropriate location to indicate that the strap is failing to perform its function of wicking static electricity properly from the wearer's body.

Other objects, features and advantages of this invention will be apparent in the specification, claims and drawings herein.

BRIEF DESCRIPTION OF THE DRAWINGS

FIG. 1 is a perspective view of a first embodiment of a device according to the present invention, comprising a strap with stretchable conductive fabric portion on which monitoring circuitry and visual and aural warning indicators are mounted.

FIG. 2 is an exploded perspective view of a second embodiment of a device according to the prestnt invention comprising a strap of metallic links on which circuitry for monitoring the performance of the strap and visual and aural warning indicators are mounted.

DETAILED DESCRIPTION OF THE DRAWINGS

Figure 3:
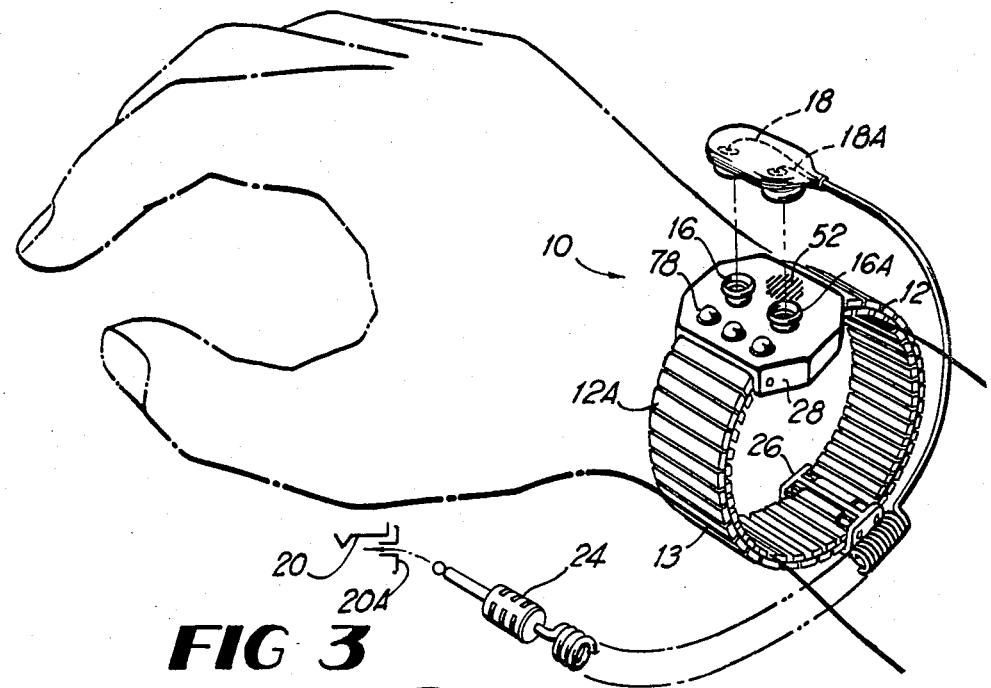
FIG. 3 is another perspective view of the strap of FIG. 2.

FIG. 1 illustrates a first embodiment of a device according to this invention. Strap 10 includes two or more sections 12 and 12A of conductive material for contacting the wearer's body. Sections 12 and 12A may be formed of conductive stainless steel or other metallic fibers, carbon-suffused synthetics, coated polymers or other conductors interwoven with nonconductive fabric as described in my co-pending patent application No. 06/804,052 entitled STRETCHABLE GROUNDING STRAP HAVING REDUNDANT CONDUCTIVE SECTIONS and my earlier U.S. Pat. No. 4,577,256 issued Mar. 18, 1986 and entitled WOVEN STRETCHABLE GROUNDING STRAP, which documents are incorporated by this reference. Sections 12 and 12A of conductive material may be placed in sectors about the periphery of strap 10 as shown in FIG. 1, or they may be placed parallel to one another as shown, for instance, in FIG. 4. Alternatively, sections 12 and 12A may be formed of metallic links 14 as shown in FIGS. 2. and 3. Sections 12 and 12A provide independent sources of contact with the wearer's body and thus allow strap 10 to establish at least two redundant routes by which static electricity may be conducted or wicked from the wearer's body. Although the drawings show straps 10 having only two sections 12 and 12A, more sections 12 and 12A may be added for further redundancy.

Conductive sections 12 and 12A are electrically connected to fasteners 16 and 16A, respectively, which may be snap connections or similar connections.

Grounding cords 18 and 18A are connected to fasteners 16 and 16A respectively and form a portion of the electrical paths between each of sections 12 or 12A of conductive material and ground. Grounding cords 18 and 18A are each connected to a receptacle 20 and 20A or ground by banana plugs 22 and 22A. Other types of plugs or connectors may be used including a two section banana plug 24 as shown in FIG. 2, or swivel-type connectors to reduce the wear and tear to grounding cords 18 and 18A resulting from undue flexion as they protrude from banana plugs 22 and 22A.

Connective sections 12 or 12A of strap 10 may be physically and electrically separated or isolated from one another by a combination of one or more isolators 26, one or more clasps 28, or simply by sections of other nonconductive material. Isolators 26 and clasps 28 should be made of anti-static material to minimize risk of inadvertent electrical contact of an isolator 26 or clasp 28 with an electrical power source and subsequent electrocution of the wearer, while simultaneously avoiding undesirable generation of static electricity on the isolator 26 or clasp 28 that could occur if they were made of insulative material. Yet they should be made of material hard enough to capture the fabric material 13 of strap 10 firmly and resiliently enough to be sufficiently durable. In the embodiment of FIG. 1, isolator 26 and clasp 28 are of nylon, which because of its hygroscopic properties is anti-static, but other suitable polymeric materials may be used.

Clasp 28 also conveniently serves as a mounting base for fasteners 16 and 16A which receive grounding cords 18 and 18A. In the embodiment shown in FIG. 1, a free swivel snap or fastener 16 and 16A are physically connected to the outer surface of clasp 28 by a rivet 30 and 30A passing through openings 32 in clasp 28. Metallic plates 34 and 34A connect conductive sections 12 and 12A electrically to rivets 30 and 30A and thus to fastener 16 and 16A. Metallic plates 34 and 34A may be of any suitable corrosion resistant metal, and serve as additional electrical contacts with the wearer's wrist. In the embodiment of FIG. 1, plates 34 and 34A are of stainless steel.

Each grounding cord may be provided with a one megohm safety resistor or a safety resistor of another suitable resistance to absorb power in the event that its corresponding grounding cord 18 or 18A inadvertently contacts a high voltage electrical source which presents a risk of electrocution to the wearer. Such resistors 36 and 36A are preferably located adjacent to portions of the cords 18 and 18A which receive fasteners 16 and 16A in order to be interposed electrically between the wearer and the dangerous electrical source. They may, of course, be electrically interposed between fasteners 16 and 16A and conductive sections 12 and 12A and be physically mounted in clasp 28 or at another suitable location.

The circuitry of the present invention is electrically connected to conductive sections 12 and 12A and thus to the electrical paths connecting them to ground.

Figure 5:
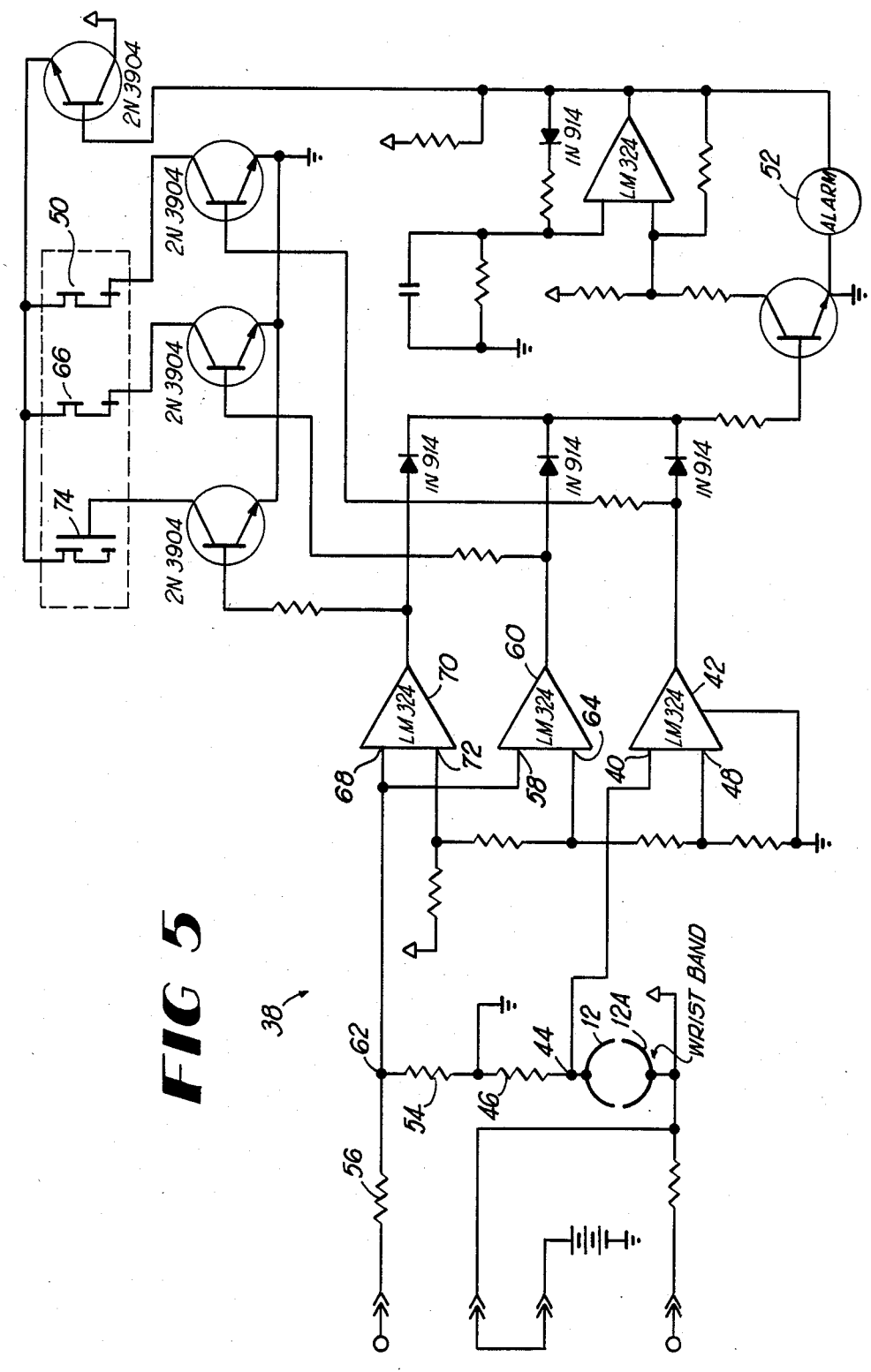
FIG. 5 is a schematic illustration showing one embodiment of circuitry of the present invention for monitoring performance of a grounding strap and its contact with electrical ground.

A schematic illustration of a preferred embodiment of circuit 38 is shown in FIG. 5. As shown in that figure, a small voltage is applied to one electrical path between conductive section 12A and ground. Interposed in the other path between the other conductive section 12 and ground are a series of resistors. The negative terminal 40 of a first operational amplifier 42 is connected to a first node 44 located between conductive section 12 and a first resistor 46. Voltage on the positive terminal 48 of first operational amplifier 42 is set to a low value according to the value of the first resistor 46 so that if resistance across conductive sections 12 and 12A, which is in the range of between $10^7$ and $10^8$ ohms under normal conditions, increases because of loss of contact with one of those sections with the wearer's body, voltage on negative terminal 40 drops below the minimum value on the positive terminal causing operational amplifier 42 to send a signal to actuate first strap visual indicator 50 and aural indicator 52.

Second and third resistors 54 and 56 are located in the path between section 12 and ground sequentially downline from the first resistor 46. The negative terminal 58 of a second operational amplifier 60 is connected to a second node 62 in the path between conductive section 12 and ground, between second resistor 54 and third resistor 56. The positive terminal 64 of second operational amplifier 60 is set at a low voltage. If the loop comprising the paths connecting the circuit 38 and ground (and thus the the paths connecting the conductive sections 12 and 12A and ground) is broken, voltage on the negative terminal of second operational amplifier 60 falls to zero and second operational amplifier sends a second ground wire open warning signal to actuate second visual indicator 66 and aural indicator 52.

Also connected to second node 62 in the electrical path between section 12 of conductive material and ground is the positive terminal 68 of third operational amplifier 70. The negative terminal 72 of third operational amplifier70 is set to a low voltage. If one of safety resistors 36 or 36A in the paths between section 12 or 12A of conductive material and ground, respectively, are shorted, the voltage on positive terminal 68 of third operational amplifier 70 increases and third amplifier sends a safety resistor short warning signal to actuate third visual indicator 74 and aural indicator 52.

Visual indicators 50, 66 and 74 may be light emitting diodes, liquid crystal displays, bulbs or other suitable visual indicators. They may be conveniently located on clasp 28, at a remote location or in both places. Similarly, aural indicator 52, a piezoelectric buzzer or screamer or other suitable device which can be heard may be located on clasp 28, at a remote location or in both places. Instead of three separate visual indicators 50, 66 and 74, one visual device may be used. It may be a single LED, LCD or bulb, or it may be another suitable device such as one which generates text which can be read by the wearer or other interested person to indicate how the device has failed. It is not always necessary to provide both a visual and aural warning indicator, and either may be omitted.

Circuit 38 conveniently may be miniaturized. For instance, operational amplifiers 42, 60 and 70 may be commercially obtained in the form of a quadruple operational amplifier semiconductor chip which may be integrated into a circuit of suitable size to place in clasp 28. Alternatively, circuit 38 may be reduced to a suitable size on a single semi-conductor chip and placed in clasp 28.

Figure 4:
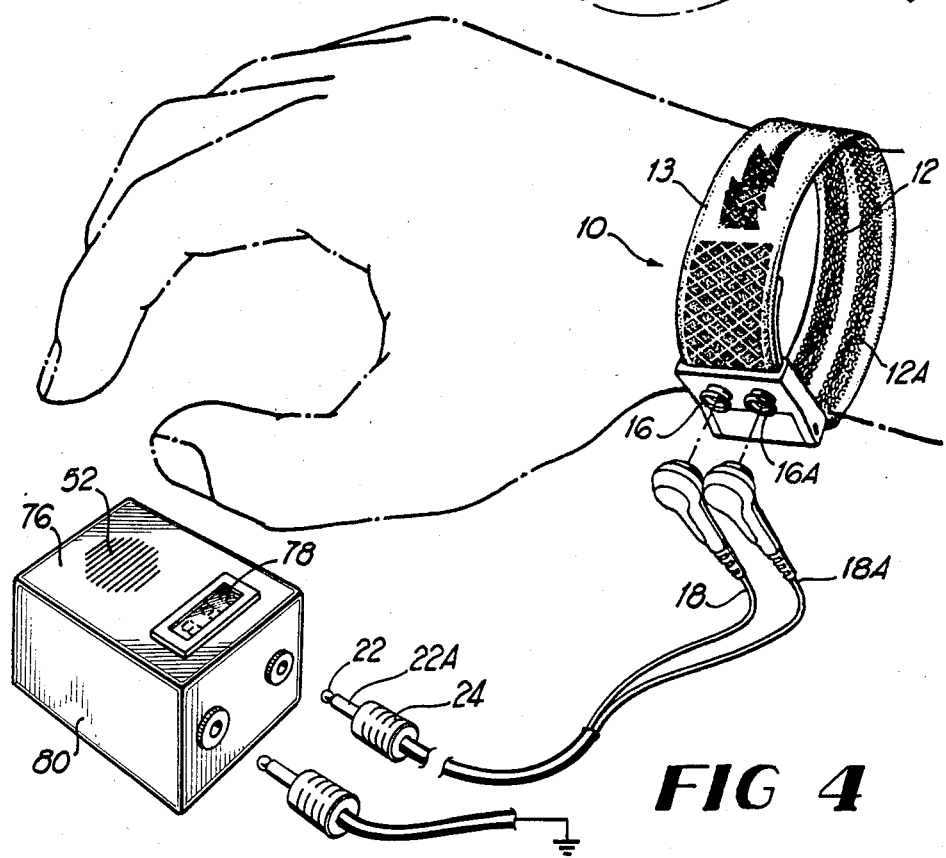
FIG. 4 is a perspective view of a third embodiment of a device according to the present invention comprising a strap of stretchable material with parallel conductive sections on the interior surface and monitoring circuitry with visual and aural warning indicators which are located remote from the strap.

Portions of circuit 38 such as visual indicator 50, 66 and 74, together with aural indicator 52, may be located remotely to be monitored at a central monitoring station. Circuit 38 may drive such indicators located in or near the strap as well as at remote locations. Circuit 38 may also be located in or near the vicinity of the strap, but apart from clasp 28 or at a remote location in an effort to minimize the cost of strap 10 by eliminating circuitry 38 from it. For instance, circuit 38 may be located in a housing at the wearer's work station into which grounding cords 18 and 18A are plugged, or in a separate housing 76 as shown in FIG. 4. The modifications to circuit 38 required by such placement resulting from, among other things, safety resistors 36 and 36A being between circuit 38 and strap 10 rather than between circuit 38 and ground, are evident.

FIGS. 2 and 3 show a strap 10 of metallic links 14 forming sections 12 and 12A of conductive material. These sections are electrically isolated from each other by isolator 26 and clasp 28. Clasp 28 contains visual indicators 50, 66 and 74, together with aural indicator 52. This version of the device is particularly appropriate for "clean room" environments in which the presence of stray metallic fibers must be minimized.

FIG. 4 shows a third embodiment of the device of the present invention. Sections 12 and 12A of conductive material are parallel to one another and are connected to fasteners 16 and 16A on clasp 28. Clasp 28 is adjustable as disclosed in my U.S. Pat. No. 4,577,256 mentioned above. Circuit 38 is located in housing 76, located remote from strap 10 or clasp 28. A visual LCD display 78 forms textual messages which indicate whether the device is operating normally, or, in the event of failure, how the device has failed. Housing 76 may also contain an aural indicator 52.

The foregoing description of this invention if for purposes of explanation and illustration. It would be apparent to those skilled in the relevant art that modifications and changes may be made to the invention as thus described without departing from its scope and spirit.

I claim:

1. A device for connecting a person's body to electrical ground, comprising:
   a. a strap which may be connected to the person's body, comprising at least two electrically conductive sections;
   b. at least two electrically connective means, each for connecting a conductive section of the strap to ground; and
   c. circuit means connected to the electrically connective means for actuating a first warning means when any of the conductive sections is not connected to ground and a second warning means when any of the conductive sections is not connected to the person's body.

2. A device according to claim 1 in which the circuit means comprises a circuit which actuates the first warning means when resistance of the loop comprising the electrically connective means connecting the circuit and the conductive sections with ground reaches a ground loop warning predetermined resistance level, and the second warning means when resistance between the electrically conductive sections of the strap reaches a strap warning predetermined resistance level.

3. A device according to claim 1 in which the electrically connective means comprises at least one conductor connecting each electrically conductive section of the strap to ground.

4. A device according to claim 1 in which at least one of the warning means is audible.

5. A device according to claim 1 in which at least one of the warning means comprises a visual indicator.

6. A device according to claim 1 in which the warning means comprises a first visual indicator means actuated when the loop connecting the circuit and ground is open and a second visual indicator means actuated when either of the conductive sections of the strap is not connected to the person's body.

7. A device according to claim 1 in which the device further comprises at least one safety resistance in the electrical path between each conductive section of the strap and ground, and the circuit means actuates a third warning means when a safety resistance is shorted.

8. A device according to claim 7 in which the third warning means is audible.

9. A device according to claim 7 in which the warning means comprise a first visual indicator actuated when the loop connecting the circuit and ground is open; a second visual indicator actuated when either of the conductive sections of the strap is not connected to the person's body; and a third visual indicator actuated when a safety resistance is shorted.

10. A device according to claim 1 in which the circuit means is mounted on the strap.

11. A device according to claim 1 in which the warning means are mounted on the strap.

12. A device for connecting a person's body to electrical ground, comprising:
   a. a strap which may be connected to the person's body, comprising at least two electrically conductive sections;
   b. at least one electrical path connecting each electrically conductive section of the strap to ground;
   c. a plurality of warning means for providing notification relating to operation of the device; and
   d. circuit means for actuating a first of the warning means when electrical resistance of any of the paths connecting the conductive sections of the strap and ground reaches a ground path warning predetermined resistance level, and a second of the warning means when electrical resistance between the electrically conductive sections of the strap reaches a strap warning predetermined resistance level.

13. A device according to claim 12 in which at least one of the warning means is audible.

14. A device according to claim 12 in which the warning means comprise a first visual indicator actuated when electrical resistance of the paths connecting the conductive sections of the strap and ground reaches a ground path warning predetermined resistance level, and a second visual indicator actuated when electrical resistance between the electrically conductive sections of the strap reaches a strap warning predetermined resistance level.

15. A device according to claim 12 in which the device further comprises at least one safety resistance in the electrical path between each conductive section of the strap and ground, and the circuit means actuates a third warning means when a safety resistance is shorted.

16. A device according to claim 12 in which the circuit means is mounted on the strap.

17. A device according to claim 12 in which the warning means are mounted on the strap.

18. A device for connecting a person's body to electrical ground, comprising:
   a. a strap which may be connected to the person's body, comprising at least two electrically conductive sections;
   b. at least one electrical path connecting each electrically conductive section of the strap to ground;
   c. at least one safety resistance in the path between each of the conductive sections of the strap and ground;
   d. a plurality of warning means for providing notification relating to operation of the device; and
   e. circuit means for actuating a first of the warning means when electrical resistance of the paths connecting the conductive sections of the strap and ground reaches a ground path warning predetermined resistance level; a second of the warning means when electrical resistance between the electrically conductive sections of the strap reaches warning predetermined resistance level; and a third of the warning means when a safety resistance is shorted.

19. A device according to claim 18 in which the warning means is audible.

20. A device according to claim 18 in which the warning means comprise a first visual indicator actuated when electrical resistance of the paths connecting the conductive sections of the strap and ground reaches a ground path warning predetermined resistance level; a second visual indicator actuated when electrical resistance between the electrically conductive sections of the strap reaches a strap warning predetermined resistance level; and a third visual indicator actuated when a safety resistance is shorted.

21. A device according to claim 18 in which the circuit means is mounted on the strap.

22. A device according to claim 18 in which the warning means are mounted on the strap.

* * * * *